US008921366B2

(12) United States Patent
Harbeson

(10) Patent No.: US 8,921,366 B2
(45) Date of Patent: *Dec. 30, 2014

(54) SUBSTITUTED TRIAZOLO-PYRIDAZINE DERIVATIVES

(71) Applicant: Concert Pharmaceuticals, Inc., Lexington, MA (US)

(72) Inventor: Scott L. Harbeson, Cambridge, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/846,119

(22) Filed: Mar. 18, 2013

(65) Prior Publication Data

US 2013/0225590 A1    Aug. 29, 2013

Related U.S. Application Data

(63) Continuation of application No. 13/174,662, filed on Jun. 30, 2011, now Pat. No. 8,399,467, which is a continuation of application No. 12/550,346, filed on Aug. 28, 2009, now Pat. No. 8,003,646.

(60) Provisional application No. 61/093,293, filed on Aug. 29, 2008.

(51) Int. Cl.
*A61K 31/50* (2006.01)
*A61K 31/495* (2006.01)
*C07D 487/04* (2006.01)

(52) U.S. Cl.
USPC .......................... 514/248; 544/236; 435/375

(58) Field of Classification Search
CPC ..... A61K 31/50; A61K 31/495; C07D 487/04
USPC ................ 514/248, 250; 544/236; 548/262.2; 435/375
See application file for complete search history.

(56) References Cited

U.S. PATENT DOCUMENTS

| | | | |
|---|---|---|---|
| 5,753,665 A | 5/1998 | Sargent et al. | |
| 6,221,335 B1 | 4/2001 | Foster | |
| 6,255,305 B1 | 7/2001 | Broughton et al. | |
| 6,440,710 B1 | 8/2002 | Keinan et al. | |
| 6,500,828 B1* | 12/2002 | Carling et al. | 514/248 |
| 6,603,008 B1 | 8/2003 | Ando et al. | |
| 6,828,322 B2* | 12/2004 | Carling et al. | 514/248 |
| 7,517,990 B2 | 4/2009 | Ito et al. | |
| 8,003,646 B2* | 8/2011 | Harbeson | 514/248 |
| 8,399,467 B2* | 3/2013 | Harbeson | 514/250 |
| 2002/0165217 A1 | 11/2002 | Howard | |
| 2006/0013770 A1* | 1/2006 | Mikkelsen | 424/9.2 |
| 2007/0082929 A1 | 4/2007 | Gant et al. | |
| 2007/0197695 A1 | 8/2007 | Potyen et al. | |
| 2008/0103122 A1 | 5/2008 | Veltri | |

FOREIGN PATENT DOCUMENTS

| | | |
|---|---|---|
| RU | 2136684 | 9/1999 |
| WO | WO-95/26325 | 10/1995 |
| WO | WO-2006/061428 | 6/2006 |
| WO | WO-2007/118651 | 10/2007 |

OTHER PUBLICATIONS

McMahon et al., Psychopharmacology (Berlin, Germany) (2007), 192(1),135-145.*
Foster, A.B., "Deuterium isotope effects in studies of drug metabolism", TIPS 524-527 (Dec. 1984).
Gouyette, A., Biomedical and Environmental Mass Spectrometry, vol. 15, 243-247 (1988).
Cherrah, Y. et al., Biomedical and Environmental Mass Spectrometry, vol. 14, Issue 11, pp. 653-657 (1987).
Dyck, L.E. et al., Journal of Neurochemistry, vol. 46, Issue 2, pp. 399-404 (1986).
Tonn, G.R., et al., Biological Mass Spectrometry, vol. 22, Issue 11, pp. 633-642 (1993).
Haskins, N.J., Biomedical Spectrometry, vol. 9, Issue 7, pp. 269-277 (1982).
Wolen, R.L., J. Clin. Pharmacology 26: 419-424 (1986).
Pieniaszek, H.J. et al., J. Clin. Pharmacol. 39:817-825 (1999).
Honma, S. et al., Drug Metab Dispos 15(4): 551-559 (1987).
Browne, T.R., Journal of Clinical Pharmacology 38: 213-220 (1998).
Baillie, T.A., Pharmacology Rev. 33:81-132 (1981).
Foster, A.B., Adv Drug Res, 14:1-40 (1985).
Fisher et al., The complexities inherent in attempts to decrease drug clearance by blocking sites of CYP-mediated metabolism. Curr Opin Drug Discov Devel. 9(1): 101-9 (2006).
Kushner, et al., "Pharmacological uses and perspectives of heavy water and deuterated compounds", Can. J. Physiol. Pharmacol. 77: 79-88 (1999).
Scott-Stevens et al., "Rodent pharmacokinetics and receptor occupancy of the GABAA receptor subtype selective benzodiazepine site ligand L-838417", Biopharm. Drug Dispos., vol. 26, No. 1, pp. 13-20 (2005).
International Preliminary Report on Patentability for corresponding PCT Application No. PCT/US2009/055427 (Dated Mar. 1, 2011).
International Search Report for corresponding PCT Application No. PCT/US2009/055427 (Dated Oct. 15, 2009).
Written Opinion for corresponding PCT Application No. PCT/US2009/055427 (Dated Oct. 15, 2009).
McMahon et al., Psychopharmacology, 192(1), 135-145 (2007).

(Continued)

*Primary Examiner* — Paul V. Ward
(74) *Attorney, Agent, or Firm* — Edwards Wildman Palmer LLP; Jeffrey D. Hsi

(57) ABSTRACT

This invention relates to novel substituted triazolo-pyridazines, their derivatives, and pharmaceutically acceptable salts thereof. This invention also provides compositions comprising a compound of this invention and the use of such compositions in methods of treating diseases and conditions that are beneficially treated by administering an α1-GABA-A receptor antagonist and/or a α2, α3 and α5 GABA-A receptor agonist.

9 Claims, 4 Drawing Sheets

(56) References Cited

OTHER PUBLICATIONS

Eurasian Search Report in corresponding Eurasian Patent Application No. 201100409, mailed Mar. 11. 2012.
Knabl et al., Nature, 451:330-335 (2008).
Nickolls et al., Advances in Pharmacological Sciences, vol. 2011, Article ID 608912, 12 pages (2011).
McKernan et al., "Sedative but not anxiolytic properties of benzodiazepines are mediated by the $GABA_A$ receptor $\alpha_1$ subtype", Nat. Neurosci., vol. 1.3, No. 6, pp. 587-592 (2000).
Notice of Reasons for Rejection mailed Mar. 26, 2013, in corresponding Japanese Patent Application No. 2013-004449.
Atack, J. R. et al., "Benzodiazepine Binding Site Occupancy by the Novel GABAA Receptor Subtype-Selective Drug 7-(1,1-Dimethylethyl)-6-(2-ethyl-2H-1,2,4-triazol-3-ylmethoxy)-3-(2-fluorophenyl)-1,2,4-triazolo[4,3-b]pyridazine (TPA023) in Rats, Primates, and Humans", Journal of Pharmacology and Experimental Therapeutics, 332(1):17-25 (2010).
Excerpt from the Prospectus (SEC Form 424B4) of Concert Pharmaceuticals, Inc., pp. 102-111, accessed at http://www.sec.gov/Archives/edgar/data/1367920/000119312514051487/d580302d424b4.htm (Feb. 2014).

* cited by examiner

SUBSTITUTED TRIAZOLO-PYRIDAZINE DERIVATIVES

CROSS-REFERENCE TO RELATED APPLICATIONS

This application is a continuation of U.S. patent application Ser. No. 13/174,662, filed Jun. 30, 2011, pending, which is a continuation of U.S. patent application Ser. No. 12/550,346, filed on Aug. 28, 2009, now U.S. Pat. No. 8,003,646, which claims the benefit of priority under 35 USC §119 to U.S. Provisional Application Ser. No. 61/093,293, filed on Aug. 29, 2008. The contents of each of the foregoing applications are incorporated herein by reference.

This invention relates to novel substituted triazolo-pyridazines, their derivatives, and pharmaceutically acceptable salts thereof. This invention also provides compositions comprising a compound of this invention and the use of such compositions in methods of treating diseases and conditions that are beneficially treated by administering an α1-GABA-A receptor antagonist.

L-838417, also known as 7-tert-butyl-3-(2,5-difluorophenyl)-6-(1-methyl-1H-1,2,4-triazol-5-ylmethoxy)[1,2,4]triazolo[4,3-b]pyridazine, acts at the benzodiazepine site of the GABA-A receptor as an antagonist of α1 subtypes, and as a functionally selective allosteric agonist of the α2, α3 and α5 subtypes.

L-838417 is currently a preclinical candidate for central nervous system disorders. Despite the beneficial activities of L-838417, there is a continuing need for new compounds that are α1-GABA-A receptor antagonists.

DEFINITIONS

Figure 1:
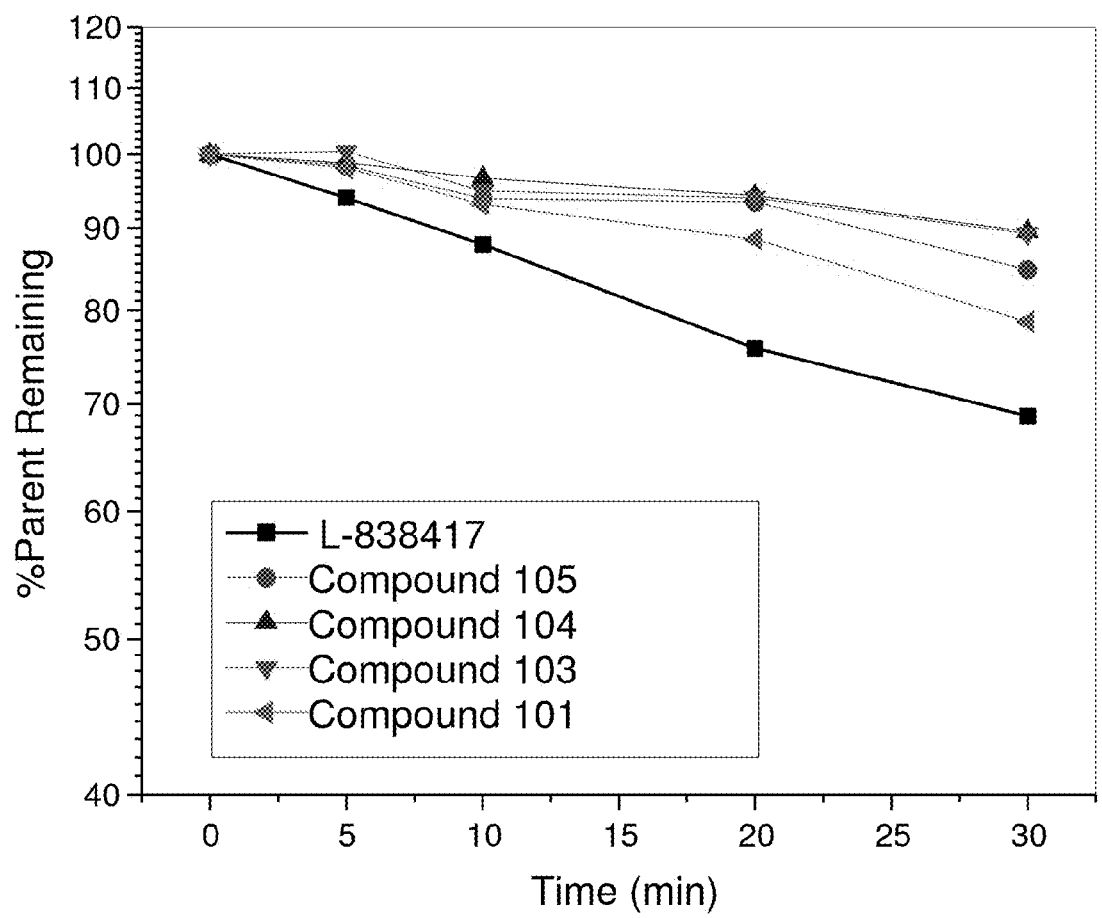
FIG. 1 depicts the stability of compounds of the invention in human liver microsomes over time.

The term "treat" means decrease, suppress, attenuate, diminish, arrest, or stabilize the development or progression of a disease (e.g., a disease or disorder delineated herein).

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of L-838417 will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725. In a compound of this invention, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3000 (45% deuterium incorporation) at each atom designated as deuterium in said compound.

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopologue" refers to a species that differs from a specific compound of this invention only in the isotopic composition thereof.

The term "compound," as used herein, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues will be less than 49.9% of the compound.

The invention also includes salts of the compounds disclosed herein.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium. "Stereoisomer" refers to both enantiomers and diastereomers. "Tert", "$^t$", and "t-" each refer to tertiary. "US" refers to the United States of America.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula I:

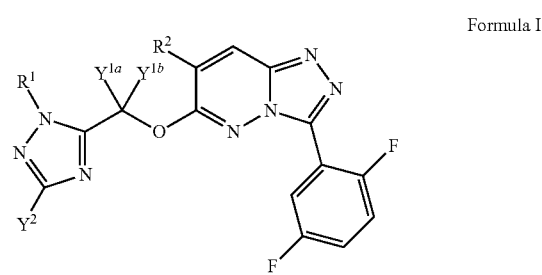

Formula I or a pharmaceutically acceptable salt thereof, wherein:
$R^1$ is $CH_3$, $CDH_2$, $CD_2H$, or $CD_3$;
$R^2$ is a t-butyl group having 0-9 deuterium atoms;
each Y is independently hydrogen or deuterium; and
when $R^1$ is $CH_3$ and each Y is hydrogen, then $R^2$ has 1-9 deuterium atoms.

One embodiment of this invention provides a compound of Formula I wherein $R^1$ is $CH_3$ or $CD_3$. In one aspect of this embodiment, $Y^{1a}$ and $Y^{1b}$ are hydrogen. In another aspect, $Y^{1a}$ and $Y^{1b}$ are deuterium. In another aspect, $Y^2$ is hydrogen. In another aspect, $Y^2$ is deuterium. In another aspect, $R^2$ is —$C(CH_3)_3$ or —$C(CD_3)_3$. As an example of this aspect, $R^2$ is —$C(CD_3)_3$.

Another embodiment provides compounds wherein $R^2$ is —$C(CH_3)_3$ or —$C(CD_3)_3$. As an example, $R^2$ is —$C(CD_3)_3$. In one aspect of this embodiment, $Y^{1a}$ and $Y^{1b}$ are hydrogen. In another aspect, $Y^{1a}$ and $Y^{1b}$ are deuterium. In another aspect, $Y^2$ is hydrogen. In another aspect, $Y^2$ is deuterium.

Another embodiment provides compounds wherein $Y^{1a}$ and $Y^{1b}$ are the same. In one aspect of this embodiment, $Y^{1a}$ and $Y^{1b}$ are deuterium. In one aspect of this embodiment, $R^2$ is —$C(CD_3)_3$.

In yet another embodiment, the compound is selected from any one of the compounds set forth in Table 1 below.

TABLE 1

Examples of Compounds of Formula I

| Compound | $R^1$ | $R^2$ | $Y^{1a}$ | $Y^{1b}$ | $Y^2$ |
|---|---|---|---|---|---|
| 101 | $CD_3$ | —$C(CH_3)_3$ | D | D | H |
| 102 | $CH_3$ | —$C(CD_3)_3$ | D | D | H |
| 103 | $CH_3$ | —$C(CD_3)_3$ | H | H | H |
| 104 | $CD_3$ | —$C(CD_3)_3$ | H | H | H |
| 105 | $CD_3$ | —$C(CD_3)_3$ | D | D | H |
| 106 | $CD_3$ | —$C(CH_3)_3$ | H | H | H |
| 107 | $CH_3$ | —$C(CH_3)_3$ | D | D | H |
| 108 | $CD_3$ | —$C(CH_3)_3$ | D | D | D |
| 109 | $CH_3$ | —$C(CD_3)_3$ | D | D | D |
| 110 | $CH_3$ | —$C(CD_3)_3$ | H | H | D |
| 111 | $CD_3$ | —$C(CD_3)_3$ | H | H | D |
| 112 | $CD_3$ | —$C(CD_3)_3$ | D | D | D |

TABLE 1-continued

Examples of Compounds of Formula I

| Compound | $R^1$ | $R^2$ | $Y^{1a}$ | $Y^{1b}$ | $Y^2$ |
|---|---|---|---|---|---|
| 113 | $CD_3$ | —$C(CH_3)_3$ | H | H | D |
| 114 | $CH_3$ | —$C(CH_3)_3$ | D | D | D |

In certain embodiments, the compound is selected from any one of Compounds 102, 103, 104, 105, 109, 110, 111 and 112, or pharmaceutically acceptable salts thereof. In other embodiments, the compound is selected from any one of Compounds 102, 103 and 105, or pharmaceutically acceptable salts thereof. In one aspect, the compound is selected from Compound 103 or Compound 105, or pharmaceutically acceptable salts thereof.

In another set of embodiments, any atom not designated as deuterium in any of the embodiments set forth above is present at its natural isotopic abundance.

The synthesis of compounds of Formula I can be readily achieved by synthetic chemists of ordinary skill following the Exemplary Synthesis and Examples disclosed herein. Other relevant procedures and intermediates are disclosed, for instance in PCT patent publication Nos. WO 98/04559 and WO 00/44752.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Certain intermediates can be used with or without purification (e.g., filtration, distillation, sublimation, crystallization, trituration, solid phase extraction, and chromatography).

Exemplary Synthesis

Compounds of Formula I may be prepared according to the schemes shown below.

Scheme 1.
General Route to Compounds of Formula I

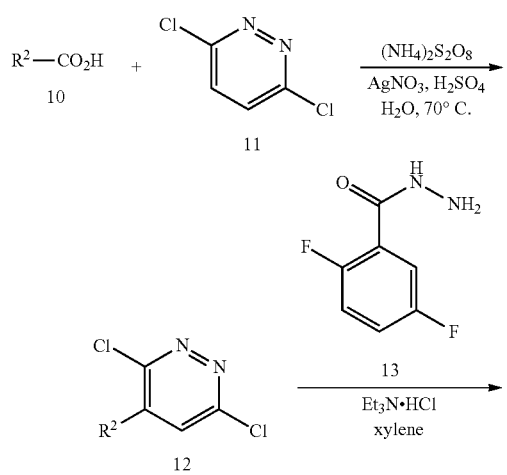

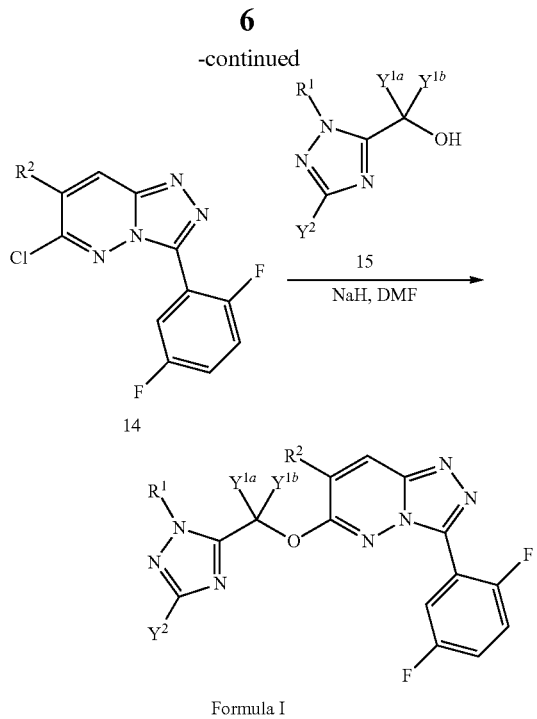

Formula I

The synthesis of compounds of Formula I can be accomplished generally as shown in Scheme 1. Intermediate 12 is prepared by radical alkylation of 3,6-dichloropyridazine 11 with the appropriately deuterated pivalic acid 10. D9-Pivalic acid is commercially available for the preparation of those compounds wherein $R^2$ is —$C(CD_3)_3$. The appropriately deuterated 3,6-dichloro-4-t-butylpyridazine 12 is then condensed with 2,5-difluorobenzohydrazide 13 to provide 14. Displacement of the chloride with the anion generated from appropriately deuterated (2-methyl-2H-1,2,4-triazol-3-yl)methanol 15 and NaH provides compounds of Formula I. Alternatively, the conversion of 14 to compounds of Formula I is accomplished via the use of n-BuLi in THF, or cesium carbonate in DMSO, or under other similar conditions known to the skilled artisan.

Scheme 2.
Synthesis of Compound 15.

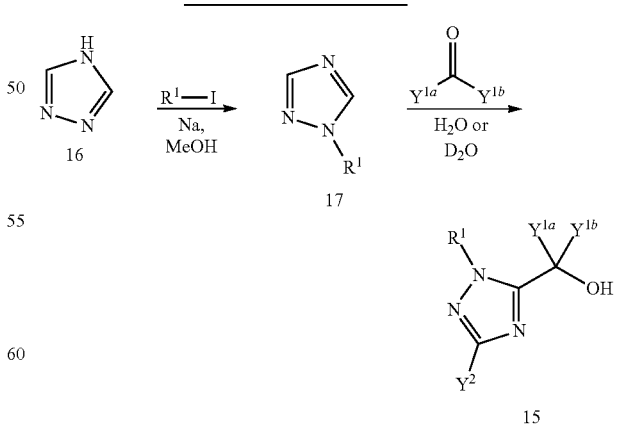

Scheme 2 illustrates the preparation of deuterated analogs of 15. As described by Dallacker F et al, Chemiker-Zeitung 1986, 110:101-108 and Dallacker F et al, Chemiker-Zeitung 1986, 110, p. 275-281, 1,2,4-triazole (16) reacts with $R^1$—I to provide the appropriately deuterated methyl triazole 17, which is then treated with formaldehyde or deuterated formaldehyde to provide 15. One skilled in the art will appreciate that deuterium exchange may potentially occur under these conditions to afford compounds wherein $Y^2$ is deuterium.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, 3$^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free compositions comprising an effective amount of a compound of Formula I (e.g., including any of the formulae herein), or a pharmaceutically acceptable salt-of said compound; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as L-838417.

Preferably, the second therapeutic agent is an agent useful in the treatment or prevention of a disease or condition selected from disorders of the central nervous system, including anxiety and convulsions; and neuropathic, inflammatory and migraine associated pain.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from about 0.01 to about 5000 mg per treatment. In more specific embodiments the range is from about 0.1 to 2500 mg, or from 0.2 to 1000 mg, or most specifically from about 1 to 500 mg. Treatment typically is administered one to three times daily.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for L-838417.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of inhibiting the α-1 subtype of the GABA-A receptor in a cell, comprising contacting a cell with one or more compounds of Formula I herein. In another embodiment, the invention provides a method of activating one or more of the α2, α3 and α5 subtypes of the GABA-A receptor in a cell.

According to another embodiment, the invention provides a method of treating a patient suffering from, or susceptible to, a disease that is beneficially treated by L-838417 comprising the step of administering to said patient an effective amount of a compound of Formula I or salt thereof, or a composition of this invention. Such diseases are well known in the art and are disclosed in, but not limited to the following patents and published applications: WO 1998004559, WO 2000044752, WO 2006061428. Such diseases include, but are not limited to, disorders of the central nervous system, including anxiety and convulsions; and neuropathic, inflammatory and migraine-associated pain.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to said patient one or more second therapeutic agents. The choice of second therapeutic agent may be made from any second therapeutic agent known to be useful for co-administration with L-838417. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formula I for use in the treatment or prevention in a patient of a disease, disorder or symptom thereof delineated herein.

Diagnostic Methods and Kits

The compounds and compositions of this invention are also useful as reagents in methods for determining the concentration of L-838417 in solution or biological sample such as plasma, examining the metabolism of L-838417 and other analytical studies.

According to one embodiment, the invention provides a method of determining the concentration, in a solution or a biological sample, of L-838417, comprising the steps of:
a) adding a known concentration of a compound of Formula I to the solution of biological sample;
b) subjecting the solution or biological sample to a measuring device that distinguishes L-838417 from a compound of Formula I;
c) calibrating the measuring device to correlate the detected quantity of the compound of Formula I with the known concentration of the compound of Formula I added to the biological sample or solution; and
d) measuring the quantity of L-838417 in the biological sample with said calibrated measuring device; and
e) determining the concentration of L-838417 in the solution of sample using the correlation between detected quantity and concentration obtained for a compound of Formula I.

Measuring devices that can distinguish L-838417 from the corresponding compound of Formula I include any measuring device that can distinguish between two compounds that differ from one another only in isotopic abundance. Exemplary measuring devices include a mass spectrometer, NMR spectrometer, or IR spectrometer.

In another embodiment, the invention provides a method of evaluating the metabolic stability of a compound of Formula I comprising the steps of contacting the compound of Formula I with a metabolizing enzyme source for a period of time and comparing the amount of the compound of Formula I with the metabolic products of the compound of Formula I after the period of time.

In a related embodiment, the invention provides a method of evaluating the metabolic stability of a compound of Formula I in a patient following administration of the compound of Formula I. This method comprises the steps of obtaining a serum, urine or feces sample from the patient at a period of time following the administration of the compound of Formula I to the subject; and comparing the amount of the compound of Formula I with the metabolic products of the compound of Formula I in the serum, urine or feces sample.

The present invention also provides kits for use to treat disorders of the central nervous system, including anxiety and convulsions; and neuropathic, inflammatory and migraine associated pain. These kits comprise (a) a pharmaceutical composition comprising a compound of Formula I or a salt thereof, wherein said pharmaceutical composition is in a container; and (b) instructions describing a method of using the pharmaceutical composition to treat disorders of the central nervous system, including anxiety and convulsions; and neuropathic, inflammatory and migraine associated pain.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

EXAMPLES

Example 1

Synthesis of 7-(tert-Butyl-$d_9$)-3-(2,5-difluorophenyl)-6-((1-methyl-1H-1,2,4-triazol-5-yl)methoxy)-[1,2,4]triazolo[4,3-b]pyridazine (Compound 103)

Compound 103 was prepared from appropriately deuterated intermediates as generally outlined in Scheme 1 above.

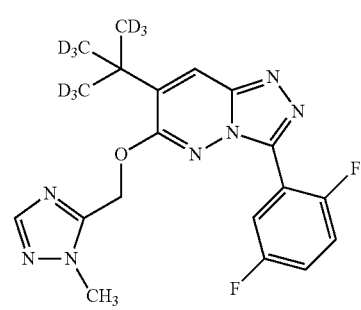

Step 1. 4-(tert-Butyl-d₉)-3,6-dichloropyridazine (12a)

Concentrated sulfuric acid (5.7 mL, 108 mmol) was added to a suspension of freshly purified 3,6-dichloro-pyridazine, 11 (5.4 g, 33.5 mmol) in distilled water (130 mL). The mixture was warmed to 65° C. and trimethylacetic acid-d₉, 10a (6.0 g, 54 mmol, CDN Isotopes, 99 atom % D) was added, followed by silver nitrate (1.1 g, 7 mmol). A solution of ammonium peroxydisulfate (12.3 g, 54 mmol) in distilled water (35 mL) was added to the mixture over a 10-15 minute period while keeping the reaction temperature at 65-75° C. The mixture was stirred for 30 minutes and cooled to room temperature. The mixture was poured onto ice (100 g) and the mixture adjusted to pH=9-10 with concentrated ammonium hydroxide. The aqueous mixture was extracted with dichloromethane (2×30 mL). The combined extracts were washed with 1N sodium hydroxide (10 mL), dried over $Na_2SO_4$, filtered and concentrated under reduced pressure. The crude product was purified by column chromatography on silica gel, eluting with 10% ethyl acetate/heptanes to give 6.1 g (80%) of 12a as a colorless oil.

Step 2. 7-(tert-Butyl-d₉)-6-chloro-3-(2,5-difluorophenyl)-[1,2,4]triazolo[4,3-b]pyridazine (14a)

A mixture of 12a (6 g, 28 mmol), 13 (7.2 g, 42 mmol, commercially available), and triethylamine hydrochloride (5.8 g, 42 mmol) in xylene (30 mL) was heated at 150° C. with stirring for 36 hours. After cooling to room temperature the mixture was concentrated under reduced pressure. The residue was triturated with dichloromethane (40 mL), filtered, and the filtrate concentrated under reduced pressure. The crude product was purified by chromatography on silica gel, eluting with 20-50% ethyl acetate/heptanes to give 5.6 g (60%) of 14a as an off-white solid.

Step 3. 7-(tert-Butyl-d₉)-3-(2,5-difluorophenyl)-6-((1-methyl-1H-1,2,4-triazol-5-yl)methoxy)-[1,2,4]triazolo[4,3-b]pyridazine (Compound 103)

To a solution of (1-methyl-1H-1,2,4-triazol-5-yl)methanol 15a (0.45 g, 4.0 mmol, commercially available) in DMF (20 mL) was added 60% sodium hydride in mineral oil (0.17, 4.3 mmol). The mixture was stirred for 15 minutes and 14a (1.2 g, 3.6 mmol) was added. The mixture was stirred for 3 hours at room temperature, then diluted with water (100 mL). The precipitate was collected by filtration and washed several times with water. The crude product was purified by column chromatography on silica gel eluting with 5% methanol/dichloromethane. The product was further purified by recrystallization from ethyl acetate-heptanes (1:1) to give 1.25 g (78%) of Compound 103 as a white solid. $^1$H-NMR (300 MHz, CDCl₃): δ 3.91 (s, 3H), 5.55 (s, 2H), 7.23-7.28 (m, 2H), 7.62-7.68 (m, 1H), 7.93 (s, 1H), 8.00 (s, 1H). $^{13}$C-NMR (75 MHz, CDCl₃): δ 34.55, 35.66, 59.37, 115.58 (dd, $J_1$=16.6, $J_2$=9.2), 117.63 (dd, $J_1$=25.8, $J_2$=6.6), 117.72 (dd, $J_1$=24.5, $J_2$=12.2), 118.72 (dd, $J_1$=24.0, $J_2$=8.5), 121.74, 137.85, 143.47, 145.00, 149.49, 151.13, 155.70 (d, J=160.9), 159.01 (d, J=155.9), 158.70. HPLC (method: Waters Atlantis T3 2.1×50 mm 3 μm C18-RP column—gradient method 5-95% ACN+0.1% formic acid in 14 min (1.0 mL/min) with 4 min hold at 95% ACN; Wavelength: 254 nm): retention time: 5.41 min; 99.3% purity. MS (M+H): 409.2. Elemental Analysis ($C_{19}H_{10}D_9F_2N_7O$): Calculated: C=55.88; H=4.69; N=24.01. Found: C=55.98; H=4.53; N=23.98.

Example 2

Synthesis of (1-(Methyl-d₃)-1H-1,2,4-triazol-5-yl)-1,1-d₂-methanol (15b)

Intermediate 15b was prepared from appropriately deuterated intermediates as generally outlined in Scheme 2 above.

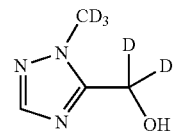

Step 1. 1-(Methyl-d₃)-1H-1,2,4-triazole (17a)

In a flask equipped with a mechanical stirrer under a nitrogen atmosphere, 1,2,4-triazole 16 (6.0 g, 87 mol) was added to anhydrous THF (60 mL) followed by the addition of iodomethane-d₃ (6.5 mL, 1.05 mol, Cambridge Isotopes, 99 atom % D). The cloudy mixture was cooled to 0° C. and 1,8-diazabicyclo[5.4.0]undec-7-ene "DBU" (13.2 mL, 0.87 mol) was added over 20 minutes. The mixture was allowed to slowly warm to room temperature and was stirred overnight. The mixture was then filtered through a Celite pad, and the filtrate concentrated under reduced pressure to give 7.3 g (>100%) of crude 17a as a yellow oil. GCMS shows a purity of 90%. The ratio of regioisomers was 12:1.

Step 2. (1-(Methyl-d₃)-1H-1,2,4-triazol-5-yl)-1,1-d₂-methanol (15b)

A mixture of 17a (5 g, 58 mmol) and paraformaldehyde-d₂ (10 g, 333 mmol, Cambridge Isotopes, 99 atom % D) was heated in a sealed tube at 170° C. for 5 hours. The mixture was cooled to room temperature and diluted with dichloromethane (20 mL). The solid was removed by filtration and the filtrate was concentrated under reduced pressure. The crude product was purified by chromatography on a short column of silica gel, eluting with 75% THF/heptanes to give 4.8 g (71%) of 15b as an off-white solid.

Example 3

Synthesis of 7-(tert-Butyl-d₉)-3-(2,5-difluorophenyl)-6-((1-(methyl-d₃)-1H-1,2,4-triazol-5-yl)-1,1-d₂-methoxy)-[1,2,4]triazolo[4,3-b]pyridazine (Compound 105)

Compound 105 was prepared from appropriately deuterated intermediates as generally outlined in Scheme 1 above.

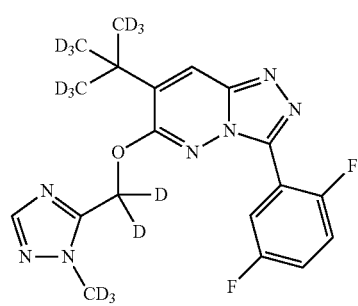

7-(tert-Butyl-d$_9$)-3-(2,5-difluorophenyl)-6-((1-(methyl-d$_3$)-1H-1,2,4-triazol-5-yl)-1,1-d$_2$-methoxy)-[1,2,4]triazolo[4,3-b]pyridazine (Compound 105)

To a solution of 15b (0.24 g, 2.0 mmol) in DMF (20 mL) was added 60% sodium hydride in mineral oil (0.08, 2.1 mmol). The mixture was stirred for 15 minutes and 14a (0.6 g, 1.8 mmol, see Example 1) was added. The mixture was stirred for 3 hours at room temperature, then diluted with water (100 mL). The precipitate was collected by filtration and washed several times with water. The crude product was purified by column chromatography on silica gel eluting with 5% methanol/dichloromethane. The product was further purified by recrystallization from ethyl acetate/heptane (1:1) to give 0.52 g (70%) of Compound 105 as a white solid. $^1$H-NMR (300 MHz, CDCl$_3$): δ 7.23-7.28 (m, 2H), 7.63-7.67 (m, 1H), 7.92 (s, 1H), 8.00 (s, 1H). $^{13}$C-NMR (75 MHz, CDCl$_3$): absence of signals at 35.66 and 59.37. HPLC (method: Waters Atlantis T3 2.1×50 mm 3 μm C18-RP column—gradient method 5-95% ACN+0.1% formic acid in 14 min (1.0 mL/min) with 4 min hold at 95% ACN; Wavelength: 254 nm): retention time: 5.40 min; 99.0% purity. MS (M+H): 414.3. Elemental Analysis (C$_{19}$H$_5$D$_{14}$F$_2$N$_7$O): Calculated: C=55.20; H=4.63; N=23.72; F=9.19. Found: C=54.88; H=4.45; N=23.46; F=9.59.

Example 4

Synthesis of (1-(Methyl-d$_3$)-1H-1,2,4-triazol-5-yl)-methanol (15c)

Intermediate 15c was prepared from appropriately deuterated intermediates as generally outlined in Scheme 2 above.

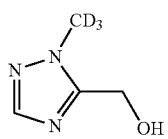

(1-(Methyl-d$_3$)-1H-1,2,4-triazol-5-yl)-methanol (15c)

A mixture of 17a (5 g, 58 mmol, see Example 2) and paraformaldehyde (10 g, 333 mmol) was heated in a sealed tube at 170° C. for 5 hours. The mixture was cooled to room temperature and diluted with dichloromethane (20 mL). The solid was removed by filtration and the filtrate was concentrated under reduced pressure. The crude product was purified by chromatography on a short column of silica gel, eluting with 5% methanol/dichloromethane to give 5.0 g (75%) of 15c as an off-white solid.

Example 5

Synthesis of 7-(tert-Butyl-d$_9$)-3-(2,5-difluorophenyl)-6-((1-(methyl-d$_3$)-1H-1,2,4-triazol-5-yl)-methoxy)-[1,2,4]triazolo[4,3-b]pyridazine (Compound 104)

Compound 104 was prepared from appropriately deuterated intermediates as generally outlined in Scheme 1 above.

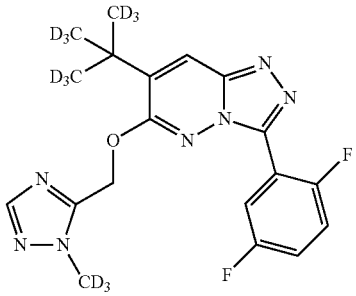

7-(tert-Butyl-d$_9$)-3-(2,5-difluorophenyl)-6-((1-(methyl-d$_3$)-1H-1,2,4-triazol-5-yl)-methoxy)-[1,2,4]triazolo[4,3-b]pyridazine (Compound 104)

To a solution of 15c (0.46 g, 4.0 mmol) in DMF (20 mL) was added 60% sodium hydride in mineral oil (0.17, 4.3 mmol). The mixture was stirred for 15 minutes and 14a (1.2 g, 3.6 mmol, see Example 1) was added. The mixture was stirred for 3 hours at room temperature, then diluted with water (100 mL). The precipitate was collected by filtration and washed several times with water. The crude product was purified by column chromatography on silica gel eluting with 5% methanol/dichloromethane. The product was further purified by recrystallization from ethyl acetate/heptane (1:1) to give 1.31 g (88%) of Compound 104 as a white solid. $^1$H-NMR (300 MHz, CDCl$_3$): δ 5.55 (s, 2H), 7.23-7.28 (m, 2H), 7.62-7.67 (m, 1H), 7.93 (s, 1H), 8.00 (s, 1H). $^{13}$C-NMR (75 MHz, CDCl$_3$): δ 34.55, 59.36, 115.53 (dd, J$_1$=16.6, J$_2$=8.8), 117.63 (dd, J$_1$=24.4, J$_2$=12.8), 117.71 (dd, J$_1$=24.1, J$_2$=8.0), 118.77 (dd, J$_1$=23.9, J$_2$=8.5), 121.75, 137.85, 143.48, 145.00, 149.50, 151.15, 155.76 (d, J=163.5), 159.08 (d, J=156.9), 158.71. HPLC (method: Waters Atlantis T3 2.1×50 mm 3 μm C18-RP column—gradient method 5-95% ACN+0.1% formic acid in 14 min (1.0 mL/min) with 4 min hold at 95% ACN; Wavelength: 254 nm): retention time: 5.40 min; 99.6% purity. MS (M+H): 412.2. Elemental Analysis (C$_{19}$H$_7$D$_{12}$F$_2$N$_7$O): Calculated: C=55.47; H=4.67; N=23.83. Found: C=55.49; H=4.76; N=23.87.

Example 6

Synthesis of 7-tert-Butyl-3-(2,5-difluorophenyl)-6-((1-(methyl-d$_3$)-1H-1,2,4-triazol-5-yl)-1,1-d$_2$-methoxy)-[1,2,4]triazolo[4,3-b]pyridazine (Compound 101)

Compound 101 was prepared from appropriately deuterated intermediates as generally outlined in Scheme 1 above.

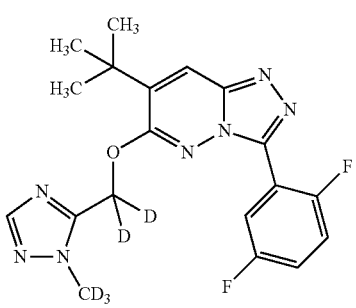

7-tert-Butyl-3-(2,5-difluorophenyl)-6-((1-(methyl-d$_3$)-1H-1,2,4-triazol-5-yl)-1,1-d$_2$-methoxy)-[1,2,4]triazolo[4,3-b]pyridazine (Compound 101)

To a solution of 15b (0.24 g, 4.0 mmol, see Example 2) in DMF (10 mL) was added 60% sodium hydride in mineral oil (0.08, 2.1 mmol). The mixture was stirred for 15 minutes and known compound 7-tert-butyl-6-chloro-3-(2,5-difluorophenyl)-[1,2,4]triazolo[4,3-b]pyridazine, 14b (0.58 g, 1.8 mmol, prepared as described in patent application WO1998004559) was added. The mixture was stirred for 3 hours at room temperature, then diluted with water (100 mL). The precipitate was collected by filtration and washed several times with water. The crude product was purified by column chromatography on silica gel eluting with 75% THF/heptanes. The product was further purified by recrystallization from ethyl acetate/heptane (1:1) to give 0.53 g (72%) of Compound 101 as a white solid. $^1$H-NMR (300 MHz, CDCl$_3$): δ 1.41 (s, 9H), 7.23-7.28 (m, 2H), 7.62-7.68 (m, 1H), 7.92 (s, 1H), 8.00 (s, 1H). $^{13}$C-NMR (75 MHz, CDCl$_3$): appearance of signal at 28.96, absence of signal at 35.66 and 59.36. HPLC (method: Waters Atlantis T3 2.1×50 mm 3 μm C18-RP column—gradient method 5-95% ACN+0.1% formic acid in 14 min (1.0 mL/min) with 4 min hold at 95% ACN; Wavelength: 254 nm): retention time: 5.42 min; 99.7% purity. MS (M+H): 405.3. Elemental Analysis (C$_{19}$H$_{14}$D$_5$F$_2$N$_7$O): Calculated: C=56.43; H=4.74; N=24.25; F=9.40. Found: C=56.22; H=4.73; N=23.87; F=9.35.

Example 7

Evaluation of Metabolic Stability

Human liver microsomes (20 mg/mL) and rat liver microsomes (20 mg/mL) were obtained from Xenotech, LLC (Lenexa, Kans.). β-nicotinamide adenine dinucleotide phosphate, reduced form (NADPH), magnesium chloride (MgCl$_2$), and dimethyl sulfoxide (DMSO) were purchased from Sigma-Aldrich.

Determination of Metabolic Stability:

7.5 mM stock solutions of test compounds (L-838417, Compound 101, Compound 103, Compound 104 and Compound 105) were prepared in DMSO. The 7.5 mM stock solutions were diluted to 12.5 μM in acetonitrile (ACN). The 20 mg/mL liver microsomes (either human or liver) were diluted to 2.5 mg/mL in 0.1 M potassium phosphate buffer, pH 7.4, containing 3 mM MgCl$_2$. The diluted microsomes (375 μL) were added to wells of a 96-well deep-well polypropylene plate in triplicate. 10 μL of the 12.5 μM test compound was added to the microsomes and the mixture was pre-warmed for 10 minutes. Reactions were initiated by addition of 125 μL pre-warmed NADPH solution. The final reaction volume is 0.5 mL and contained 0.5 mg/mL human liver microsomes, 0.25 μM test compound, and 2 mM NADPH in 0.1 M potassium phosphate buffer, pH 7.4, and 3 mM MgCl$_2$. The reaction mixtures are incubated at 37° C., and 50 μL aliquots were removed at 0, 5, 10, 20, and 30 minutes and added to shallow-well 96-well plates which contained 50 μL of ice-cold ACN with internal standard to stop the reactions. The plates were stored at 4° C. for 20 minutes after which 100 μL of water was added to the wells of the plate before centrifugation to pellet precipitated proteins. Supernatants were transferred to another 96-well plate and analyzed for amounts of parent remaining by LC-MS/MS using an Applied Bio-systems API 4000 mass spectrometer. 7-ethoxycoumarin (1 μM) was used as a positive control.

Data Analysis:

The in vitro $t_{1/2}$s for test compounds were calculated from the slopes of the linear regression of % parent remaining (ln) vs incubation time relationship, using the formula:

in vitro $t_{1/2}$=0.693/k, where k=−[slope of linear regression of % parent remaining(ln) vs incubation time]

Data analysis is performed using Microsoft Excel Software.

The results of these experiments are shown in FIGS. 1 (human liver microsomes) and 2 (rat liver microsomes). As shown in FIG. 1, approximately 70% of L-838417 remained intact after 30 minutes of incubation with human liver microsomes. The half life of L-838417 was calculated to be 54.4 minutes. In contrast, each of Compounds 101, 103, 104 and 105 were stable in human liver microsomes (more than 80% of parent compound remained intact after 30 minute incubation).

Figure 2:
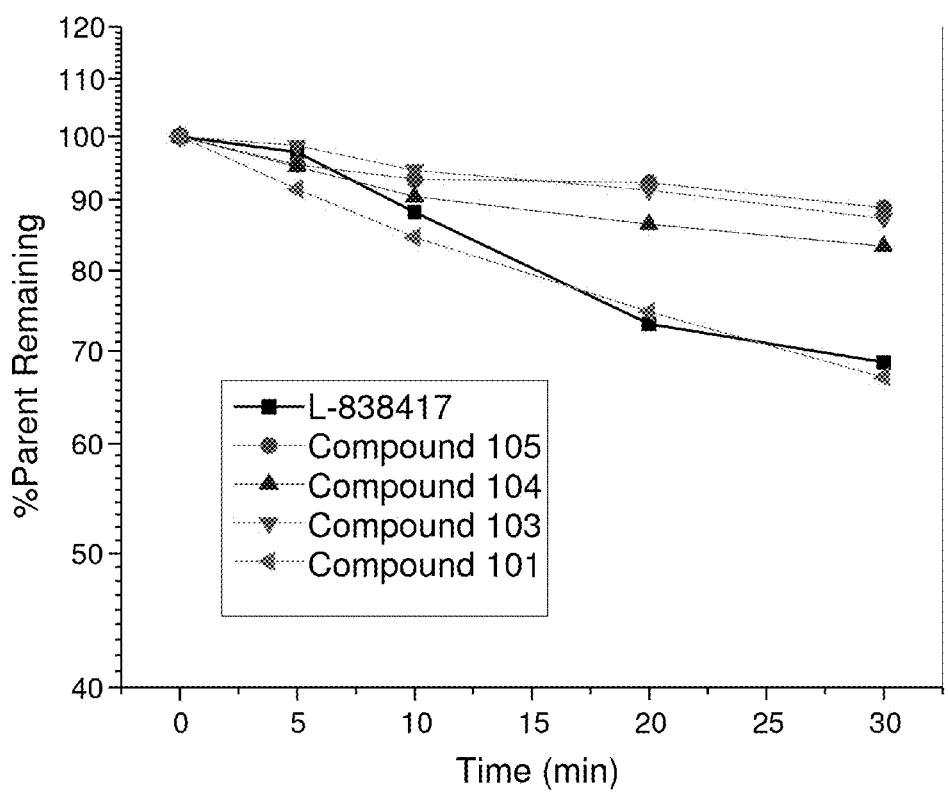
FIG. 2 depicts the stability of compounds of the invention in rat liver microsomes over time.

In rat liver microsomes, approximately 70% of both L-838417 and Compound 101 remained intact after 30 minutes of incubation (FIG. 2). The calculated half-lives were 50.5 minutes for L-838417 and 52.7 minutes for Compound 101. More than 80% of each of Compounds 103, 104 and 105 remained intact after 30 minutes of incubation, and each was considered stable in rat microsomes.

Example 8

Pharmacokinetic and Bioavailability Analysis of Compounds 103 and 105 Following Oral and Intravenous Administration to Rats Three male Sprague-Dawley rats (200-250 g each) were cannulated in the jugular vein and were administered a single dose containing 1 mg/kg each of L-838417, Compound 103 and Compound 105 (as a 1:1:1 mixture containing 1 mg/mL of each of the three compounds in 10% dimethyl sulfoxide (DMSO), 10% N,N-dimethylacetamide (DMA), and 60% polyethylene glycol (PG) through the jugular cannula. Three additional male Sprague-Dawley rats (200-250 g each) were administered a single dose containing 1 mg/kg each of L-838417, Compound 103 and Compound 105 (as a 1:1:1 mixture containing 1 mg/mL of each of the three compounds in 10% dimethyl sulfoxide (DMSO), 10% N,N-dimethylacetamide (DMA), and 60% polyethylene glycol (PG) by oral gavage.

Blood (0.25 mL) from intravenously treated test rats was collected retro-orbitally at 2, 5, 15, and 30 minutes, and 1, 2, 4, and 6 hours post-dosing. Blood (0.25 mL) from orally treated test rats was collected retro-orbitally at 5, 15, 30, and 45 minutes, and 1, 2, 4, and 6 hours post-dosing. Blood was collected into tubes containing K$_2$EDTA as anticoagulant at the above mentioned time points. Blood samples were stored on ice and then centrifuged to obtain plasma. The plasma (~0.125 μL) was aliquoted into deep 96-well plates and stored at −80° C. until analysis by LC-MS/MS using an Applied Bio-systems API 4000 mass spectrometer.

Figure 3:
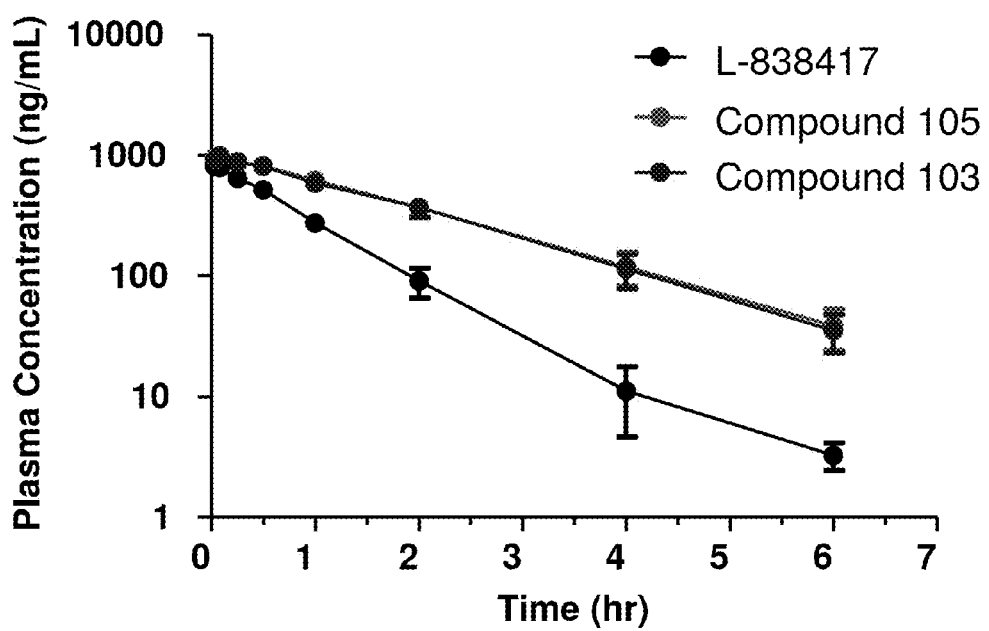
FIG. 3 depicts the change in concentration of compounds of the invention in plasma following intravenous administration to rats.

The results of the intravenous portion of this study are shown in FIG. 3 and in Table 2, below.

TABLE 2

Pharmacokinetics of L-838417, Compound 103 and Compound 105 after Intravenous Administration to Sprague-Dawley Rats.

|  | L-838417 | Compound 103 | % Change over L-838417 | Compound 105 | % Change over L-838417 |
| --- | --- | --- | --- | --- | --- |
| $t_{1/2}$ (hr) | 0.7 ± 0.04 | 1.25 ± 0.14 | +79 | 1.27 ± 0.14 | +81 |
| CL (L/hr/kg) | 1.1 ± 0.11 | 0.48 ± 0.05 | −62 | 0.46 ± 0.05 | −60 |
| $AUC_{0-6}$ (hr * ng/mL) | 831 ± 86 | 1920 ± 200 | +131 | 1957 ± 190 | +136 |

These results demonstrate that Compounds 103 and 105 each have an approximately 80% longer half-life and produce a greater than two-fold higher $AUC_{0-6}$ than undeuterated L-838417 following intravenous administration to rats. In addition, both Compound 103 and 105 are each cleared approximately 60% more slowly than L-838417.

Figure 4:
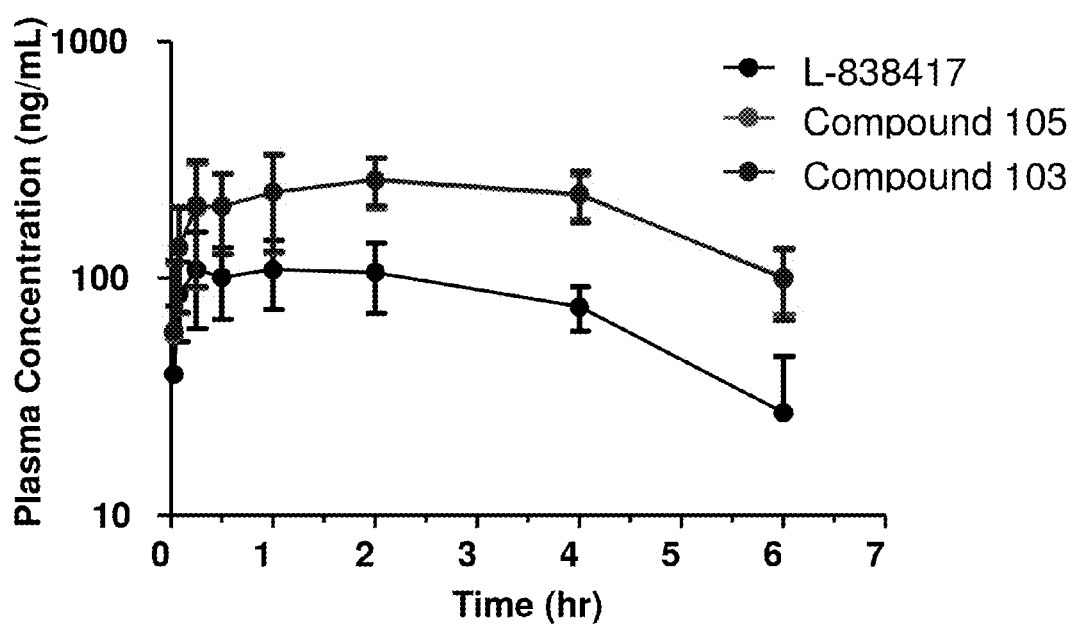
FIG. 4 depicts the change in concentration of compounds of the invention in plasma following oral administration to rats.

The results of the oral administration portion of this study are shown in FIG. 4 and in Table 3, below.

TABLE 3

Pharmacokinetics of L-838417, Compound 103 and Compound 105 after Oral Administration to Sprague-Dawley Rats.

|  | L-838417 | Compound 103 | % Change over L-838417 | Compound 105 | % Change over L-838417 |
| --- | --- | --- | --- | --- | --- |
| $C_{max}$ (ng/mL) | 128 ± 40 | 277 ± 76 | +116 | 280 ± 80 | +119 |
| $AUC_{0-6}$ (hr * ng/mL) | 491 ± 95 | 1258 ± 289 | +156 | 1248 ± 272 | +154 |

These results show that Compounds 103 and 105 demonstrate a greater than two-fold higher $C_{max}$ following oral administration in rats than L-838417. In addition, the results show that Compounds 103 and 105 produce a greater than two and a half-fold higher $AUC_{0-6}$ than undeuterated L-838417 following oral administration.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound of Formula I:

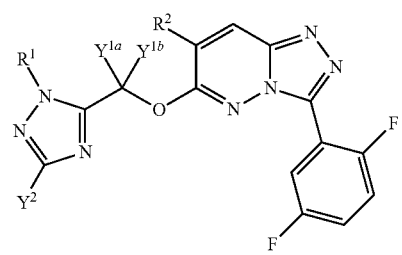

Formula I or a pharmaceutically acceptable salt thereof, wherein:
$R^1$ is $CH_3$ or $CD_3$;
$R^2$ is —$C(CD_3)_3$;
$Y^{1a}$ and $Y^{1b}$ are the same and are selected from hydrogen or deuterium;
$Y^2$ is hydrogen or deuterium; and
the compound has at least 90% deuterium incorporation at each position designated as deuterium.

2. The compound of claim 1, selected from:

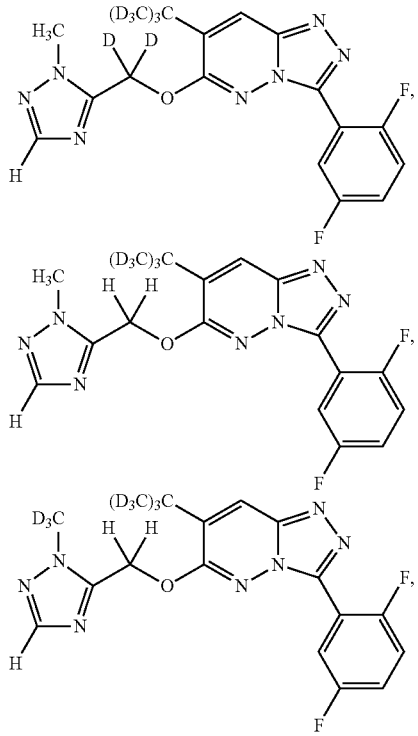

-continued

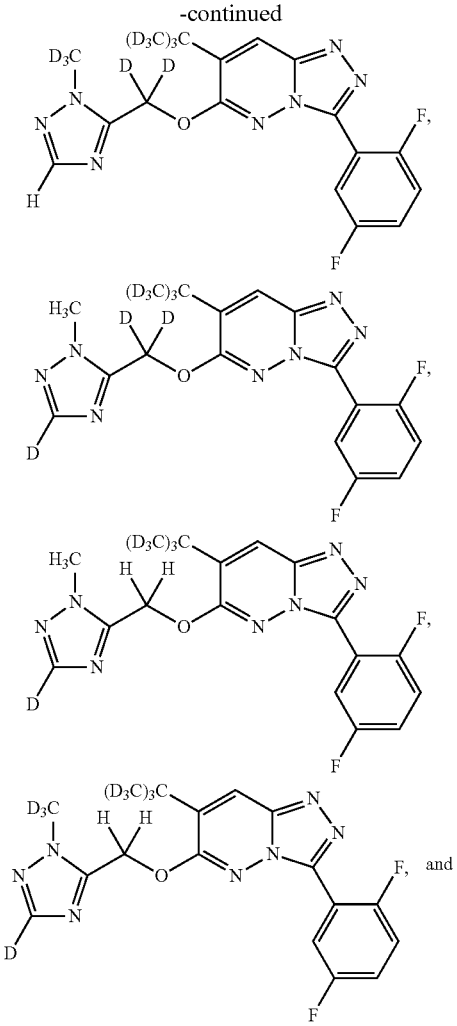

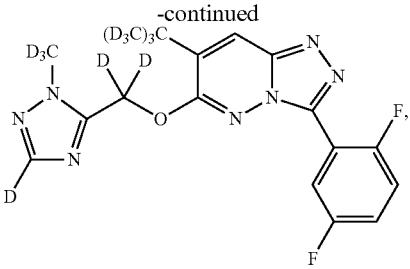

or a pharmaceutically acceptable salt thereof.

3. The compound of claim 1, wherein the compound has at least 95% deuterium incorporation at each position designated as deuterium.

4. The compound of claim 1, wherein the compound has at least 97% deuterium incorporation at each position designated as deuterium.

5. The compound of claim 1, wherein any atom not designated as deuterium is present at its natural isotopic abundance.

6. A pyrogen-free pharmaceutical composition comprising a compound of claim 1, or a pharmaceutically acceptable salt thereof; and a pharmaceutically acceptable carrier.

7. A method of:
   a. inhibiting the α-1 subtype of the GABA-A receptor in a cell; or
   b. activating one or more of the α2, α3 and α5 subtypes of the GABA-A receptor in a cell,
the method comprising contacting the cell with a compound of claim 1.

8. A method of treating a patient suffering from a disease or condition selected from neuropathic pain, inflammatory pain, and migraine pain, comprising the step of administering to the patient in need thereof a composition of claim 6.

9. A method of treating a patient suffering from anxiety or convulsions, the method comprising the step of administering to the patient in need thereof a pharmaceutical composition of claim 6.

\* \* \* \* \*